United States Patent
Mitsunaga et al.

(10) Patent No.: US 7,416,784 B2
(45) Date of Patent: Aug. 26, 2008

(54) FUNCTIONAL INFRARED FLUORESCENT PARTICLE

(75) Inventors: Masakazu Mitsunaga, Osaka (JP); Naoki Usuki, Osaka (JP); Kenji Kohno, Osaka (JP); Hisao Kanzaki, Osaka (JP); Mikio Kishimoto, Osaka (JP)

(73) Assignee: Hitachi Maxell, Ltd., Osaka (JP)

( * ) Notice: Subject to any disclaimer, the term of this patent is extended or adjusted under 35 U.S.C. 154(b) by 0 days.

(21) Appl. No.: 11/633,504

(22) Filed: Dec. 5, 2006

(65) Prior Publication Data
US 2007/0161786 A1   Jul. 12, 2007

(30) Foreign Application Priority Data
Dec. 6, 2005 (JP) ............ P2005-352405

(51) Int. Cl.
*B32B 5/16* (2006.01)
(52) U.S. Cl. ............ 428/403; 977/773; 977/811
(58) Field of Classification Search .......... 428/403; 977/773, 811
See application file for complete search history.

(56) References Cited

U.S. PATENT DOCUMENTS

| | | | |
|---|---|---|---|
| 5,611,958 A | | 3/1997 | Takeuchi et al. |
| 5,932,139 A | * | 8/1999 | Oshima et al. ......... 252/301.16 |
| 6,268,222 B1 | * | 7/2001 | Chandler et al. ............ 436/523 |
| 6,309,701 B1 | * | 10/2001 | Barbera-Guillem ...... 427/213.3 |
| 6,703,248 B1 | * | 3/2004 | Singh et al. .................. 436/518 |
| 6,846,565 B2 | * | 1/2005 | Korgel et al. ............... 428/402 |
| 6,964,747 B2 | * | 11/2005 | Banerjee et al. .............. 264/4.1 |
| 2004/0126902 A1 | | 7/2004 | Nishiya et al. |

FOREIGN PATENT DOCUMENTS

| | | |
|---|---|---|
| JP | 3336572 B2 | 8/2002 |
| JP | 2004-31792 A | 1/2004 |

* cited by examiner

*Primary Examiner*—H. T Le
(74) *Attorney, Agent, or Firm*—Birch, Stewart, Kolasch & Birch, LLP.

(57) ABSTRACT

An infrared fluorescent particle comprising a functional group or a substance that is capable of binding to an analyte, wherein fluorescence at infrared wavelength is emitted from the particle upon exposure of the particle to excitation light at infrared wavelength. The infrared fluorescent particle of the present invention is capable of binding to the analyte. Due to a high penetration of the fluorescence and the excitation light into biological substances; the infrared fluorescent particle of the present invention can reduce an influence of luminescence, light absorption or light scattering which is occurred due to the analyte and the surrounding substances.

11 Claims, No Drawings

FUNCTIONAL INFRARED FLUORESCENT PARTICLE

CROSS REFERENCE TO RELATED PATENT APPLICATION

The present application claims the right of priority of Japanese Patent Application No. 2005-352405 (filed Dec. 6, 2005, the title of the invention: "INFRARED FLUORESCENT FUNCTIONAL PARTICLE"), the disclosure of which is incorporated herein by reference in its entirety.

FIELD OF THE INVENTION

The present invention relates to an infrared fluorescent particle (which can be also called "particle made of an infrared fluorescent material") that is suitable for use in a biological or biochemical field such as an imaging technology. In particular, the present invention relates to the infrared fluorescent particle capable of binding to an analyte wherein fluorescence at near-infrared wavelength is emitted from the particle upon exposure of the particle to excitation light at near-infrared wavelength.

BACKGROUND OF THE INVENTION

At present, there is a technology called "imaging" or "imaging technology". In the imaging technology, some fluorescent material is injected into a biological body followed by the aggregation of the fluorescent material near a particular area of the body, and then the aggregated fluorescent material is observed from outside the body. For this reason, the fluorescent material is expected as a useful material in the imaging technology. In this technology, not only safety and stability are required for the fluorescent material, but also a high penetrating power of excitation light and fluorescence to biological materials is required. From this point of view, an organic fluorescent material that emits light having from ultraviolet wavelengths to visible wavelengths as well as a quantum dot-substance, for example, has problems with a fluorescent stability, a toxicity and a penetrability of fluorescence.

The present invention is directed to solve the above problems. That is to say, an object of the present invention is to provide a favorable fluorescent particle in terms of a penetration of fluorescence and excitation light into biological materials so that the particle can be suitably used in the imaging technology and the like.

SUMMARY OF THE INVENTION

In order to achieve the object, the present invention provides an infrared fluorescent particle comprising a functional group or a substance that is capable of binding to an analyte, wherein fluorescence at infrared wavelength is emitted from the particle upon exposure of the particle to excitation light at infrared wavelength.

The infrared fluorescent particle of the present invention is capable of emitting or generating fluorescence having an infrared wavelength region (particularly near-infrared wavelength region) upon exposure of the particle to excitation light having an infrared wavelength region (particularly near-infrared wavelength region). The infrared fluorescent particle of the present invention is also capable of binding to an analyte since the particle comprises a functional group or a substance capable of binding to such analyte. As a result, such infrared fluorescent particle can be used as a fluorescent probe of the imaging technology. As described above, the infrared fluorescent particle of the present invention has a variety of useful functions, and for this reason the particle of the present invention can be called "functional infrared fluorescent particle".

Due to a high penetration of infrared light into biological substances, the infrared fluorescent particle of the present invention can reduce an influence of luminescence, light absorption or light scattering which may be occurred by the analyte and the surrounding substances. This results in a low background, which will lead to a higher substantive sensitivity. In the case where the infrared particle is made of a metal oxide, stable fluorescence intensity can be obtained. That is to say, the fluorescence intensity does not decrease during exposure of the particle to the excitation light. In addition, the infrared fluorescent particle of the present invention in itself has a low toxicity. Therefore, the infrared fluorescent particle, which is made of the metal oxide according to the present invention, is particularly useful for imaging the analyte that is surrounded by a variety of biological substances. Further, such infrared fluorescent particle is also particularly useful for imaging a particular tissue that exists within a biological body.

DETAILED DESCRIPTION OF THE PREFERRED EMBODIMENTS

Hereinafter, the infrared fluorescent particle of the present invention will be described in more detail.

As used in this specification and claims, the phrase "infrared fluorescent particle" means a particle that is capable of radiating light energy at infrared wavelength(s) upon exposure of the particle to the excitation light at infrared wavelength(s). In a case where the particle radiates light energy in a very short period of time upon exposure to the excitation light, such light energy is considered to be radiated in the form of "fluorescence". In contrast, in a case where the particle radiates light energy in a longer period of time, such light energy is considered to be radiated in the form of "phosphorescence". Therefore, "infrared fluorescent particle" substantially means a particle capable of radiating "fluorescence" as well as "phosphorescence".

As used in this specification and claims, the phrase "capable of binding to an analyte" substantially means that "functional group or substance" is capable of physically or chemically binding to "analyte". Thus, the meaning of this phrase includes an embodiment wherein "functional group or substance" is capable of binding to "analyte" due to "adsorption", "coulomb force" or the like.

As used in this specification and claims, the term "analyte" generally means, but is not limited to, a substance to be assayed or tested. The term "analyte" also means a substance to be merely bound to the infrared fluorescent particle for various purposes.

As used in this specification and claims, the term "particle" generally means, unless otherwise stated herein, a plurality of particles, and particularly means particles in powder form.

Not only the excitation light to which the infrared fluorescent particle is exposed has an infrared wavelength region, but also the fluorescence emitted from such particle has an infrared wavelength region. Therefore, a high penetration of the excitation light and the fluorescence into the analyte and the surrounding substances can be obtained, which will lead to a reduction in the influence of luminescence including visible fluorescence, light absorption or light scattering occurred by such analyte and surrounding substances. It is preferred that a peak wavelength of an excitation light spectrum and a peak wavelength of a fluorescence spectrum are both between 700 nm and 3000 nm. In other word, they are both within a near-infrared region. In a case where light has a wavelength region less than the near-infrared region, not only the light absorption and the luminescence having optical wavelengths are increased, but also the light scattering is increased. Meanwhile, in a case where light has a wavelength region greater than the near-infrared region, an infrared absorption by the analyte is increased. Particularly when the infrared fluorescent particle of the present invention is used for imaging the analyte in the biological substance-containing specimen, or when it is used for imaging the particular area within the living body, some water is typically present around such analyte or area. It is therefore preferred that the peak wavelength of each of the excitation light spectrum and the fluorescence spectrum is between 700 nm and 1300 nm in the near-infrared region, which will lead to a decrease in the light absorption by the water. In a case where there is a bigger difference between an excitation light wavelength and a fluorescence wavelength upon measurement of the fluorescence intensity, the influence of the excitation light can be easily reduced. It is therefore more preferred that the peak wavelength of the excitation light spectrum is between 700 nm and 1100 nm in the near-infrared region, and the peak wavelength of the fluorescence spectrum is between 850 nm and 1200 nm in the near-infrared region.

When the difference between the peak wavelength of the excitation light spectrum and the peak wavelength of the fluorescence spectrum is less than or equal to 20 nm, it is difficult to split into the excitation light and the fluorescence with the filter and the like. Even if it is possible, an overlap wavelength region between the excitation light and the fluorescent needs to be eliminated, which results in a loss of light quantity. Therefore, the difference between the peak wavelength of the excitation light spectrum and the peak wavelength of the fluorescence spectrum is preferably more than or equal to 20 nm, more preferably more than or equal to 50 nm, and the most preferably more than or equal to 100 nm.

In an embodiment of the present invention, it is preferred that, in a case where the infrared fluorescent particle of the present invention is used in the form of powder, each of infrared fluorescent particle is uniform in shape and size (i.e. diameter). In a case where the infrared fluorescent particle is used within a liquid, it is desirable that the particle can be uniformly dispersed into the liquid so that a variation of the detection is kept as low as possible. Therefore, the maximum diameter of the infrared fluorescent particle is preferably less than or equal to 5 μm, more preferably less than or equal to 500 nm, and the most preferably less than or equal to 100 nm. In the meanwhile, it is preferred that the minimum diameter of the infrared fluorescent particle is generally more than or equal to 2 nm. It should be understood that such minimum diameter is determined in terms of a manufacturability of the particle and a detectability of the fluorescence intensity. To sum up the above, it is preferred that the infrared fluorescent particle has a diameter of between 2 nm and 5 um. As used in this specification and claims, the term "diameter" means a diameter that is obtained by reading and then averaging 100 particles for example wherein such 100 particles are randomly selected from a picture image of the particles magnified by an electron microscope or optical microscope. In a case where the particle is not round in its shapes, "diameter" then means an average value of the maximum length and the minimum length of such particle. It will be understood that a preferable diameter of the particle may vary depending on a shape and kind of the analyte or the infrared fluorescent particle.

The infrared fluorescent particle of the present invention can be made of any suitable materials such as an inorganic material, an organic material, a composite material or a complex. In particular, it is preferred that the infrared fluorescent particle of the present invention is made of the inorganic material since the fluorescence intensity obtained therefrom does not decrease too much during exposure of the particle to the excitation light, and the thus particle is excellent in terms of its stability.

In an embodiment of the present invention, it is preferred that the infrared fluorescent particle is desirable from a safe or environmental point of view. For example, the infrared fluorescent particle made of a metal oxide is suitably used as the particle of the present invention since such particle generally has a high stability as well as a low toxicity. The infrared fluorescent particle made of the metal oxide may be the particle made of a chemical compound comprising a transition metal element, a phosphorus element and an oxygen element. The representative example of such chemical compound may include $Y.Nd.Yb.PO_4$, $Lu.Nd.Yb.PO_4$ and $La.Nd.Yb.PO_4$ (in which Y: Yttrium element, Nd: Neodymium element, Yb: Ytterbium element, Lu: Lutetium element, La: Lanthanum element, P: Phosphorus element and O: Oxygen element).

As the infrared fluorescent particle made of the metal oxide, the infrared fluorescent particle made of the metal oxide expressed by a composition formula $A_{1-x-y}Nd_xYb_yPO_4$ (in which A is at least one element selected from the group consisting of Y, Lu and La; $0<x\leq0.5$, $0<y\leq0.5$ and $0<x+y<1$) is particularly preferable. Furthermore, among the particles made of the metal oxide expressed by such formula, the particle having an afterglow duration time of more than or equal to 100 μs is preferable. As used in this specification, the phrase "afterglow duration time" means a time from stopping of the exposure to the excitation light until the obtained fluorescence intensity becomes one-tenth of its initial intensity.

The infrared fluorescent particle of the present invention can be used for detecting or imaging the particular area within the living body since the particle is capable of adsorbing to or binding to such area. Furthermore, even in a case where such area is located relatively deeply within the living body or even in a case where a variety of other substances are present around the analyte and the infrared fluorescent particle, the analyte can be detected or imaged through the infrared fluorescent particle. The reason for this is that both of the excitation light and the fluorescence have an infrared region, the penetrability thereof into the biological substances being relatively high.

The infrared fluorescent particle comprises a substance or a functional group that is capable of binding to the analyte. As a result, the analyte can be assayed with this particle. It is preferred that "functional group or substance that is capable of binding to an analyte" is immobilized on the infrared fluorescent particle. As used in this specification, the term "immobilized" generally means an embodiment wherein "functional group or substance that is capable of binding to an analyte" exists near the surface of the infrared fluorescent particle. For this reason, this term does not necessarily mean an embodiment wherein "functional group or substance that is capable of binding to an analyte" is in a direct contact with the surface of the infrared fluorescent particle.

In an embodiment of the present invention, it is preferred that "functional group that is capable of binding to an analyte" is at least one functional group selected from the group consisting of amino group, carboxyl group, epoxy group, thiol group, nitro group, succinimide group, maleimide group, formyl group, hydrazine group and tosyl group. In this case, the analyte having a reactiveness or an affinity for the above functional groups can bind or adsorb to the infrared fluorescent particle of the present invention. The functional groups as described above may be activated, for example by adding different kinds of catalytic agents, dehydrating agents or the like. The representative examples of the activated functional groups may be as follows:

a carboxyl group activated by adding of carbodiimide;

a carboxyl group in the form of acid anhydride; and an epoxy group activated by adding of tertiary amine or alcohol.

In an embodiment of the present invention, it is preferred that "substance that is capable of binding to an analyte" is at least one substance selected from the group consisting of silica, hydroxyapatite, ligand, receptor, antigen, antibody, biotin, avidin, protein A, protein G, nucleic acid and sugar chain. In this case, the analyte can bind or adsorb to the infrared fluorescent particle of the present invention via the above substances.

As described above, the infrared fluorescent particle of the present invention comprises the immobilized "functional group or substance that is capable of binding to an analyte" so that the particle binds to the analyte via the functional group or the substance. The analyte may be any kinds of substances. It is preferred that the analyte is at least one substance selected from the group consisting of living body tissue, microorganism and cell. Such analyte generally coexists with the other substances to form a living body or mixture, and thus the analyte is generally surrounded by the other substances. Particularly in a case where the infrared fluorescent particle of the present invention is used within the living body for the imaging, various kinds of biologically-relevant substances may be present around the analyte to be assayed. Examples of "substances that may be present around the analyte" may include a biological fluid or substance (e.g. a living body tissue, microorganism, cell and blood), water and the like.

As a method for introducing "functional group that is capable of binding to an analyte" to the infrared fluorescent particle, any types of methods can be employed. For example, it is possible to employ a method for bringing a silane coupling agent into reaction with the surface of the infrared fluorescent particle. In this method, the functional group may be directly reacted with the surface of the infrared fluorescent particle, or it may be reacted with the surface on which a silica or the like is preliminarily immobilized. There are however limits to the kind of functional group that can be immobilized with the silane coupling agent. Thus, subsequent to the introduction of a functional group with the silane coupling agent, this functional group may be highly activated through a reaction with some kind of substance. Alternatively, subsequent to the introduction of a certain functional group to the particle, another certain functional group may be introduced thereto. Instead of the silane coupling agent, a titanium coupling agent or a silazane may be used.

A substance having not only a certain functional group that can adsorb or bind to the surface of the infrared fluorescent particle but also another certain functional group to be introduced may be immobilized. For example, the following dispersant may be immobilized:

Polyethylene glycol having amino groups at both ends; and

Polyethylene glycol having an amino group at one end and a carboxyl group at the other end.

The infrared fluorescent particles may be used in the form of a micelle or a liposome so that the functional group exists at an outermost region of the micelle or liposome. Alternatively, the infrared fluorescent particle may be covered with some kind of polymer having a certain functional group (e.g. polyallylamine, chitosan or the like). Alternatively, the particle may be covered with the polymer, followed by introducing a certain functional group to such polymer. Some surfactant (e.g. Tween or Triton) may be added to a liquid which contains the infrared fluorescent particles in order to improve a dispersibility of the particles.

As a method for introducing "substance that is capable of binding to an analyte" to the infrared fluorescent particle, any types of method can be also employed. For example, a sol-gel method is available for the immobilization of the silica. A coating method as described in Japanese Patent Kokai Publication No. 2004-031792 is also suitably available, the disclosure of this publication is incorporated herein by reference. In this coating method, an appropriate amount of sodium silicate is dissolved into a water suspension that contains the infrared fluorescent particles, and subsequently the water suspension is neutralized by acid. As a result, the infrared fluorescent particles coated with a specified amount of the silica can be obtained wherein the silica is present near to the surface of each particle. In a case of the immobilization of a calcium phosphate compound (e.g. hydroxyapatite), another coating method is available. In this method, the infrared fluorescent particles are dispersed into water, and subsequently pH of the resulting dispersion liquid is adjusted by adding a calcium salt aqueous solution and a phosphoric salt aqueous solution thereto. As a result, the calcium phosphate compound is crystallized or deposited adjacent to the surface of each infrared fluorescent particle. Finally, by subjecting the particles to a hydrothermal treatment, the particles coated with the calcium phosphate compound can be obtained.

It is commonly believed that various kinds of functional groups are present on the surface of the metal oxide. Thus, simply by mixing metal oxide particles and some kind of substance (e.g. antigen, antibody, biotin, avidin, nucleic acid and/or sugar chain), such substance can be immobilized on the surface of the particle. In other words, the infrared fluorescent particle of the present invention, which is made of the metal oxide, can be obtained by such a simple method.

Furthermore, it is possible to crystallize or deposit "substance that is capable of binding to an analyte" on the surface of the infrared fluorescent particle by changing the solubility condition of such substance. In this case, the solubility condition of the substance to be immobilized is changed from a higher solubility condition to a lower solubility condition. For example, the following procedures can be performed to obtain a more reliable immobilization:

a certain functional group is preliminarily immobilized on the infrared fluorescent particle, and subsequently "the preliminarily immobilized functional group" and "functional group or substance that is capable of binding to an analyte" are bound to each other; and "Substance having not only a certain functional group but also another certain functional group capable of being immobilized to the surface of the particle" and "functional group or substance that is capable of binding to an analyte" are preliminarily bound to each other, and subsequently they are immobilized to the surface of the particle.

The present invention as described above includes the following embodiments:

The first embodiment: the infrared fluorescent particle(s) comprising a functional group or a substance that is capable of binding to an analyte, wherein fluorescence at infrared wavelength(s) is(are) emitted from said particle(s) upon exposure of said particle(s) to excitation light at infrared wavelength(s).

The second embodiment: the particle(s) according to the first embodiment, wherein said excitation light has a spectrum, a peak wavelength of said spectrum being in a near-infrared region, and said fluorescence has a spectrum, a peak wavelength of said spectrum being in a near-infrared region.

The third embodiment: the particle(s) according to the second embodiment, wherein said peak wavelength of said spectrum of said excitation light is between 700 nm and 1100 nm, and said peak wavelength of said spectrum of said fluorescence is between 850 nm and 1200 nm.

The fourth embodiment: the particle(s) according to the second or third embodiment, wherein a difference between said peak wavelength of said spectrum of said excitation light and said peak wavelength of said spectrum of said fluorescence is more than or equal to 50 nm.

The fifth embodiment: the particle(s) according to any one of the first to fourth embodiments, wherein a diameter (i.e. size) of said particle(s) is(are) between 2 nm and 5 μm.

The sixth embodiment: the particle(s) according to any one of the first to fifth embodiments, wherein the said particle(s) is(are) made of a metal oxide.

The seventh embodiment: the particle(s) according to the sixth embodiment, wherein said metal oxide comprises transition metal element, phosphorus element and oxygen element.

The eighth embodiment: the particle(s) according to the seventh embodiment, wherein said particle(s) is(are) made of said metal oxide expressed by a composition formula $A_{1-x-y}Nd_xYb_yPO_4$ (in which A is at least one element selected from the group consisting of Y, Lu and La; $0<x\leqq0.5$, $0<y\leqq0.5$ and $0<x+y<1$).

The ninth embodiment: the particle(s) according to any one of the first to eight embodiments, wherein said analyte is at least one substance selected from the group consisting of living body tissue (i.e. tissue from biological object), microorganism and cell.

The tenth embodiment: the particle(s) according to any one of the first to ninth embodiments, wherein said functional group is at least one functional group selected from the group consisting of amino group, carboxyl group, epoxy group, thiol group, nitro group, succinimide group, maleimide group, formyl group, hydrazine group and tosyl group.

The eleventh embodiment: the particle(s) according to any one of the first to ninth embodiments, wherein said substance is at least one substance selected from the group consisting of silica, hydroxyapatite, ligand, receptor, antigen, antibody, biotin, avidin, protein A, protein G, nucleic acid and sugar chain.

The present invention will be further described by reference to the following detailed examples, which are exemplary in nature and not intended to limit the scope of the invention.

《《Synthesis of Infrared Fluorescent Particle》》

EXAMPLE 1

Prior to the synthesis of the infrared fluorescent particle of the present invention, a precursor particle was synthesized according to example 1 disclosed in Japanese Patent Publication No. 3336572. This precursor particle is an infrared fluorescent particle on which "functional group or substance that is capable of binding to an analyte" has not yet been immobilized.

First, 3.5 g of $Nd_2O_3$, 4.0 g of $Yb_2O_3$, 18.0 g of $Y_2O_3$ and 60.0 g of $H_3PO_4$ were thoroughly mixed together, and the resulting mixture was charged into a crucible (such crucible was provided with an alumina lid). The mixture was then heated from a room temperature (i.e. ambient temperature) up to about 700° C. for 2 hours at constant rate of temperature rise, followed by subjecting the mixture to a calcination treatment for 6 hours at a temperature of about 700° C. These heating treatments were performed by means of an electric heating furnace wherein the crucible was set. Immediately after the calcination treatment was completed, the crucible was taken out of the electrical heating furnace and then it was allowed to stand and cool in the air. Subsequently, the crucible was immersed in hot water of 100° C. to boil it. After taking the resulting fluorescent particles out of the crucible, the particles were washed with 1N nitric acid and then water, followed by drying. As a result, the precursor particles expressed by a composition formula $Nd_{0.1}Yb_{0.1}Y_{0.8}PO_4$ were obtained. As described above, these precursor particles were the infrared fluorescent particles on which "functional group or substance that is capable of binding to an analyte" has not yet been immobilized. When the precursor particles were exposed to the excitation light whose peak wavelength was about 810 nm, the fluorescence whose peak wavelength was about 980 nm was then emitted from the precursor particles.

Subsequently 5 parts by weight of the precursor particles were dispersed into water. 1 part by weight of tetraethoxysilane and 5 parts by weight of ammonia water were respectively added to the resulting dispersion, followed by stirring to deposit or crystallize the silane on the surface of the particles. Subsequently the dispersion was subjected to centrifugation, followed by removing the resulting supernatant liquid. After that, the following washing treatments were performed repeatedly five times: water was added to the resulting particle concentrate; and then the resulting mixture was subjected to centrifugation, followed by removing the resulting supernatant liquid. Finally, by drying the resulting particles at a temperature of 100° C., the silica-immobilized infrared fluorescent particles were obtained.

EXAMPLE 2

5 parts by weight of the precursor particles obtained from Example 1 were dispersed into water/ethyl alcohol (1/1 by volume), and subsequently 1 part by weight of silane coupling agent having amino group was added to the dispersion. The resulting mixture was stirred for 1 hour, and then subjected to centrifugation, followed by removing the resulting supernatant liquid. Finally, by drying the resulting particles at a temperature of 120° C., the amino group-immobilized infrared fluorescent particles were obtained.

EXAMPLE 3

This example was performed in the same way as Example 2, except that a silane coupling agent having epoxy group was used instead of the silane coupling agent having amino group. As a result, the epoxy group-immobilized infrared fluorescent particles were obtained.

EXAMPLE 4

1 part by weight of the particles obtained from Example 3 (i.e. epoxy group-immobilized infrared fluorescent particles) were dispersed into 20 parts by weight of ethanolamine aqueous solution (5 percent by weight solution of ethanolamine), and subsequently the resulting dispersion was stirred overnight. As a result, the hydroxyl group-immobilized infrared fluorescent particles were obtained. The particles were washed repeatedly with water and acetone. Subsequently 1 part by weight of such particles were dispersed into 20 parts by weight of pyridine, followed by adding 0.2 parts by weight of tosyl chloride to the resulting dispersion. The resulting mixture was stirred overnight. Finally, after washing the resulting particles with toluene repeatedly four times, the tosyl group-immobilized infrared fluorescent particles were obtained.

EXAMPLE 5

1 part by weight of the infrared fluorescent particles obtained from Example 2 were dispersed into water. 100 parts by weight of 10 mg/ml hydrosoluble carbodiimide (1-ethyl-3-(3-dimethylaminopropyl) carbodiimide hydrochloride salt) was added to the resulting dispersion. The resulting mixture was subjected to centrifugation, followed by removing the resulting supernatant liquid. Subsequently a series of the washing treatments (i.e. adding water followed by stirring, and then centrifugation followed by removing the resulting supernatant liquid) were performed repeatedly three times. After that, PBS buffer (PBS: Phosphate buffered saline) and 0.06 parts by weight of streptavidin were added to the resulting particle concentrate so as to react the streptavidin and the particles with each other for 2 hours at a temperature of 37° C. The resulting mixture was subjected to centrifugation, followed by removing the resulting supernatant liquid. Finally, after washing the resulting particles with PBS repeatedly five times, the streptavidin-immobilized infrared fluorescent particles were obtained.

EXAMPLE 6

1 part by weight of the particles obtained from Example 3 (i.e. epoxy group-immobilized infrared fluorescent particles) were dispersed into 100 parts by weight of PBS, followed by adding 0.06 parts by weight of streptavidin to the resulting dispersion. The resulting mixture was stirred overnight. Finally, after washing the resulting particles with PBS repeatedly three times, the streptavidin-immobilized infrared fluorescent particles were obtained.

EXAMPLE 7

1 part by weight of the particles obtained from Example 4 (i.e. tosyl group-immobilized infrared fluorescent particles) were dispersed into 100 parts by weight of PBS, followed by adding 0.01 parts by weight of streptavidin to the resulting dispersion. The resulting mixture was stirred overnight. Finally, after washing the resulting particles with PBS repeatedly three times, the streptavidin-immobilized infrared fluorescent particles were obtained.

EXAMPLE 8

This example was performed in the same way as Example 2, except that the particles obtained from Example 1 (i.e. silica-immobilized infrared fluorescent particles) were used instead of the precursor particles of Example 1. That is to say, the following procedures were performed. 5 parts by weight of the silica-immobilized infrared fluorescent particles obtained from Example 1 were dispersed into water/ethyl alcohol (1/1 by volume), and subsequently 1 part by weight of silane coupling agent having amino group was added to the dispersion. The resulting mixture was stirred for 1 hour, and then subjected to centrifugation, followed by removing the resulting supernatant liquid. Finally, by drying the resulting particles at a temperature of 120° C., the amino group-immobilized infrared fluorescent particles were obtained.

EXAMPLE 9

This example was performed in the same way as Example 5, except that the particles obtained from Example 8 (i.e. amino group-immobilized infrared fluorescent particles) were used instead of the particles obtained from Example 2. That is to say, the following procedures were performed. 1 part by weight of the amino group-immobilized infrared fluorescent particles obtained from Example 8 were dispersed into water. 100 parts by weight of 10 mg/ml hydrosoluble carbodiimide (1-ethyl-3-(3-dimethylaminopropyl) carbodiimide hydrochloride salt) was added to the resulting dispersion. The resulting mixture was subjected to centrifugation, followed by removing the resulting supernatant liquid. Subsequently a series of the washing treatments (i.e. adding water followed by stirring, and then centrifugation followed by removing the resulting supernatant liquid) were performed repeatedly three times. After that, PBS buffer and 0.06 parts by weight of streptavidin were added to the resulting particle concentrate so as to react the PBS buffer and the particles with each other for 2 hours at a temperature of 37° C. The resulting mixture was subjected to centrifugation, followed by removing the resulting supernatant liquid. Finally, after washing the resulting particles with PBS repeatedly five times, the streptavidin-immobilized infrared fluorescent particles were obtained.

COMPARATIVE EXAMPLE 1

In this comparative example, the infrared fluorescent particle on which surface no functional group or no substance was immobilized was prepared. In particular, the precursor particles obtained in the course of Example 1 were used.

COMPARATIVE EXAMPLE 2

In this comparative example, the infrared fluorescent organic material on which a functional substance (i.e. streptavidin) was immobilized was prepared. In particular, an infrared fluorescent organic dye, IRDye800 Conjugated Streptavidin was used without modification.

COMPARATIVE EXAMPLE 3

In this comparative example, a visible fluorescent material on which surface no functional group or no substance was immobilized. In particular, SINLOIHI COLORBASE SW-13 containing a visible fluorescent pigment (i.e. pigment capable of emitting fluorescence having a visible region) was used without modification.

By using of the infrared fluorescent particles of Examples 1 to 9 as well as the particle and materials of Comparative examples 1 to 3, adsorption characteristic or binding characteristic thereof for the biological substances was examined.

《《Confirmatory Test of Amount of Bound or Adsorbed Analyte》》

(Confirmation Test of Amount of Adsorbed Nucleic Acid)

The following procedures were conducted in order to confirm the amount of the adsorbed nucleic acid (λ DNA) with respect to the particles of Example 1 and Comparative example 1. The procedure in the case of the infrared fluorescent particles of Example 1 will be mainly described, which is much the same for the case of the precursor particles of Comparative example 1.

(A) Preparation for Confirmation Test:
  (a) The infrared fluorescent particles of Example 1 were dispersed into the sterilized water in order to form 0.2 mg/ml dispersion liquid.
  (b) As a biological sample containing the nucleic acid to be extracted or isolated, 10 μg/100 μl λ DNA solution was prepared by diluting λ DNA (Nacalai Tesque, Inc.) with the sterilized water.
  (c) As a solution for extracting or isolating the nucleic acid, a chaotropic buffer called a buffer A [7M guanidinium hydrochloride (Nacalai Tesque, Inc.) and 50 mM Tris-HCl (SIGMA, Ltd), pH 7.5] was used.
  (d) As a washing liquid, a chaotropic buffer called a buffer A [7M guanidinium hydrochloride (Nacalai Tesque, Inc.) and 50 mM Tris-HCl (SIGMA, Ltd), pH 7.5] was used.
  (e) As a reagent for removing a highly-concentrated salt as described below, acetone solution and 70 percent by weight ethanol solution were respectively used.
  (f) As an eluent for collecting the nucleic acid adsorbed to the infrared fluorescent particle of Example 1, the sterilized water was used.

(B) Procedures of Confirmatory Test:
  (1) 1000 ul of the solution for extracting or isolating the nucleic acid (i.e. the above (c) solution) was poured into 100 ul of the λ DNA solution (i.e. the above (b) solution), followed by mixing.
  (2) 20 ul of the dispersion liquid (i.e. the above (a) dispersion liquid) was added to the resulting mixture.
  (3) The mixture was stirred every other about 2 minutes while it was allowed to stand at a room temperature for 10 minutes.
  (4) The mixture was subjected to centrifugation, so that the infrared fluorescent particles aggregated near the bottom edge of a centrifugal tube.
  (5) The supernatant liquid was removed by suck with a pipette.
  (6) 1 cc of the washing liquid containing guanidinium hydrochloride (i.e. the above (d) liquid) was supplied into the tube where the infrared fluorescent particles were present.
  (7) The washing liquid and the infrared fluorescent particles were thoroughly mixed together, and the resulting mixture was again subjected to centrifugation, followed by removing the resulting supernatant liquid by suck with the pipette.
  (8) The above washing treatments were performed repeatedly.
  (9) The infrared fluorescent particles (to which the nucleic acid binds) were washed with 1 cc of 70 percent by weight ethanol solution (i.e. the above (e) solution). As a result, a highly-concentrated guanidinium hydrochloride was removed.
  (10) The washing treatment was again performed with 1 cc of 70 percent by weight ethanol solution (i.e. the above (e) solution) and 1 cc of acetone solution (i.e. the above (e) solution).
  (11) The tube was set in Heat Block of about 56° C., and then allowed to maintain for about 10 minutes. As a result, the acetone was completely distilled off the tube and the particles.
  (12) 100 ul of the sterilized water (i.e. the above (f) water) was added to the infrared fluorescent particles (to which the nucleic acid binds) in the tube, and the tube was then set again in Heat Block of about 56° C. The resulting mixture was stirred every other about 2 minutes while the mixture was allowed to stand for 10 minutes.
  (13) The mixture was subsequently subjected to centrifugation. The resulting supernatant liquid containing the nucleic acid was sucked with the pipette, and then transferred into another tube. The volume of the collected liquid was 70 ul.
  (14) The absorbance (OD:260 nm) for the collected liquid acid was measured by means of an absorption spectrometer (JASCO Corporation, V-570) to obtain the concentration of the nucleic acid in the collected liquid. Finally, amount of the adsorbed nucleic acid (i.e. amount of nuclei acid adsorbed to the particles) was estimated from the amount of the collected nucleic acid wherein the amount of the collected nucleic acid was obtained by multiplying the concentration of the nucleic acid by the volume of the collected liquid.

(Confirmation Tests of Amount of Adsorbed Streptavidin and Biotynylated HRP)

The streptavidin-immobilized infrared fluorescent particles obtained from Examples 5, 6, 7 and 9 were respectively used. 100 ul of 20 ng/ml biotynylated HRP (horseradish peroxidase) was added to 5 ug of the particles of each Example, and the resulting mixture was then stirred for 30 minutes. 100 ul of tetramethylbenzidine (TMB) was added to the mixture, followed by allowing to stand for 30 minutes to react with each other. After stopping the reaction by adding 200 ul of 1N sulfuric acid, the color strength as an absorbance (at 450 nm wavelength) of the mixture was measured by means of an absorption spectrometer (JASCO Corporation, V-570). Finally, amounts of the adsorbed streptavidin and biotynylated HRP were respectively estimated by comparing the measured color strength with some samples of known concentration.

(Result of Confirmatory Tests)

With respect to the infrared fluorescent particles of Examples 1 to 9 as well as the particle and materials of Comparative examples 1 to 3, the estimated bound amounts or adsorbed amounts are shown in the following Table 1.

TABLE 1

| | Immobilized functional group or substance | Bound or adsorbed analyte | Amount of bound or adsorbed analyte |
|---|---|---|---|
| Example 1 | silica | λ DNA | 6.5 μg |
| Example 2 | amino group | streptavidin (Example 5) | 150 nmol/g |
| Example 3 | epoxy group | streptavidin (Example 6) | 210 nmol/g |
| Example 4 | tosyl group | streptavidin (Example 7) | 240 nmol/g |
| Example 5 | streptavidin | biotynylated HRP | 150 nmol/g |
| Example 6 | streptavidin | biotynylated HRP | 210 nmol/g |
| Example 7 | streptavidin | biotynylated HRP | 240 nmol/g |
| Example 8 | amino group | streptavidin (Example 9) | 350 nmol/g |
| Example 9 | streptavidin | biotynylated HRP | 350 nmol/g |
| Comparative example 1 | — | λ DNA | 0.7 μg |
| | — | streptavidin | 5 nmol/g |
| | — | biotynylated HRP | 5 nmol/g |
| Comparative example 2 | — | (cannot be separated by centrifugation) | — |
| Comparative example 3 | — | biotynylated HRP | 2 nmol/g |

Table 1 shows that the infrared fluorescent particles of the present invention, namely, silica-, amino group-, epoxy group-, tosyl- and streptavidin-immobilized infrared fluorescent particles are all capable of binding or adsorbing to some specific analyte as compared with the particle and material of Comparative examples 1 and 3. It can be therefore understand that the infrared fluorescent particle of the present invention is capable of binding to a biological substance, a living body or a particular area thereof.

《《Fluorescence Spectrum Measurement》》

The intensity of the fluorescence emitted from the infrared fluorescent particle (to which λ DNA, streptavidin or biotynylated HRP binds) was measured. For this measurement, an apparatus provided with several varieties of laser equipments and Si photodiode detector was used.

For the particles of Examples 1 to 9, 810 nm-laser light was used. Meanwhile, for the particle and materials of Comparative examples 1, 2 and 3, 810 nm-, 780 nm- and 532 nm-laser lights were respectively used. Each of the laser lights was filtered to use the filtered laser light as the excitation light (that is to say, the light other than the intended excitation light was eliminated by the filter for each case). In particular, the filer was arranged in front of each of the particles and materials. For the particles of Examples 1 to 9 and Comparative example 1, the filter that allows passage of light having around 980 nm wavelength was used. For the material of Comparative example 2, the filter that allows passage of light having around 810 nm wavelength was used. For the material of Comparative example 3, the filter that allows passage of light having around 590 nm wavelength was used. The Si photodiode detector was used to detect the fluorescence generated from the above particles and materials upon exposure to the excitation light.

Samples for the fluorescence measurement were prepared by dispersing or dissolving each of the particles and materials of Examples 1 to 9 and Comparative examples 1 to 3 into water, and then by dropping the resulting dispersion or solution on a membrane filter to dry it. Upon the measurement, each of the prepared samples was exposed to the excitation light.

It was confirmed that the fluorescence was strongly generated upon the exposure in each case of Examples 1 to 9 and Comparative examples 1 to 3.

Additionally, a similar fluorescence measurement was performed under such a condition that each sample was placed on a thin bull leather. That is to say, the fluorescence was measured via the thin bull leather. As a result, in each case of Examples 1 to 9 and Comparative example 1, the fluorescence was observed (each intensity of the observed fluorescence was approximately 2 orders of magnitude less than that of the above each case wherein no leather was used). In the case of Comparative example 2, the fluorescence was also observed although the intensity thereof was approximately 2 to 3 orders of magnitude less than that of the above each where no leather was used. In the case of the material of Comparative example 3, no fluorescence was observed.

Additionally, another similar fluorescence measurement was performed under such a condition that each sample was continuously exposed to 810 nm-laser light. As a result, it was confirmed that the fluorescent intensity did not decrease during exposure in each case of Examples 1 to 9 and Comparative examples 1 and 3. In contrast, it was confirmed that the fluorescence intensity decreased by a factor of 3 after exposure of about 5 minutes in the case of Example 2 (i.e. fluorescent organic dye).

To sum up all the above, the following matters could be concluded:

The fluorescence generated in each case of Examples 1 to 9 (wherein the fluorescence had an infrared region) had a penetrating power greater than that of Comparative example 3 (wherein the fluorescence had a visible region).

The decrease in fluorescence intensity upon exposure in each case of Examples 1 to 9 (wherein the infrared fluorescent particles made of metal oxide were used) was smaller than that of Comparative example 2 (wherein the fluorescent organic dye was used).

The apparatus provided with the laser equipment and Si photodiode detector was able to measure the fluorescence intensity. This means that a picture image can be obtained by scanning such fluorescence intensity.

INDUSTRIAL APPLICABILITY

Infrared region light (in particular, near-infrared region light) relating to the infrared fluorescent particle of the present invention has a high penetrating power into the biological substances and the like. In addition, the infrared fluorescent particle of the present particle is capable of binding to a particular substance.

Therefore, the infrared fluorescent particle of the present invention is suitable for use in the imaging technology wherein a particular substance or an object having such particular substance is imaged. The infrared fluorescent particle of the present invention is also suitable for use as a detection reagent or a quantitative assay reagent wherein a particular substance is detected or quantitatively assayed.

What is claimed is:

1. An infrared fluorescent particle comprising a functional group or a substance that is capable of binding to an analyte, wherein fluorescence at infrared wavelength is emitted from said particle from the region not containing said functional group or substance that is capable of binding to an analyte upon exposure of said particle to excitation light at infrared wavelength, wherein said functional group or substance that is capable of binding to an analyte is immobilized on the infrared fluorescent particle.

2. The particle according to claim 1, wherein said excitation light has a spectrum, a peak wavelength of said spectrum being in a near-infrared region, and said fluorescence has a spectrum, a peak wavelength of said spectrum being in a near-infrared region.

3. The particle according to claim 2, wherein said peak wavelength of said spectrum of said excitation light is between 700 nm and 1100 nm, and said peak wavelength of said spectrum of said fluorescence is between 850 nm and 1200 nm.

4. The particle according to claim 2, wherein a difference between said peak wavelength of said spectrum of said excitation light and said peak wavelength of said spectrum of said fluorescence is more than or equal to 50 nm.

5. The particle according to claim 1, wherein a diameter of said particle is between 2 nm and 5 μm.

6. The particle according to claim 1, wherein the said particle is made of a metal oxide.

7. The particle according to claim 6, wherein said metal oxide comprises transition metal element, phosphorus element and oxygen element.

8. The particle according to claim 7, wherein said particle is made of said metal oxide expressed by a composition formula $A_{1-x-y}Nd_xYb_yPO_4$ (in which A is at least one element selected from the group consisting of Y, Lu and La; $0<x\leqq0.5$, $0<y\leqq0.5$ and $0<x+y<1$).

9. The particle according to claim 1, wherein said analyte is at least one substance selected from the group consisting of living body tissue, microorganism and cell.

10. The particle according to claim 1, wherein said functional group is at least one functional group selected from the group consisting of amino group, carboxyl group, epoxy group, thiol group, nitro group, succinimide group, maleimide group, formyl group, hydrazine group and tosyl group.

11. The particle according to claim 1, wherein said substance is at least one substance selected from the group consisting of silica, hydroxyapatite, ligand, receptor, antigen, antibody, biotin, avidin, protein A, protein G, nucleic acid and sugar chain.

* * * * *